US005893876A

United States Patent [19]
Turkel et al.

[11] Patent Number: 5,893,876
[45] Date of Patent: Apr. 13, 1999

[54] COLPOSCOPIC BIOPSY PUNCH WITH REMOVABLE MULTIPLE SAMPLE BASKET

[75] Inventors: David Turkel, Miami; Juergen Andrew Kortenbach, Miami Springs, both of Fla.

[73] Assignee: Symbiosis Corporation, Miami, Fla.

[21] Appl. No.: 08/886,221

[22] Filed: Jul. 1, 1997

Related U.S. Application Data

[62] Division of application No. 08/355,057, Dec. 13, 1994, Pat. No. 5,643,307.

[51] Int. Cl.[6] .................................................. A61B 17/28
[52] U.S. Cl. ........................ 606/205; 600/562; 606/184
[58] Field of Search .......................... 606/205–211, 167, 606/170, 171, 174, 1, 184, 815; 600/562–567

[56] References Cited

U.S. PATENT DOCUMENTS

| 1,609,014 | 11/1926 | Dowd | 606/114 |
|---|---|---|---|
| 2,293,171 | 8/1942 | Reardon | 606/115 |
| 4,971,067 | 11/1990 | Bolduc et al. | 600/564 |
| 5,603,724 | 2/1997 | O'connor | 600/564 |

*Primary Examiner*—Glenn K. Dawson

*Attorney, Agent, or Firm*—Finnegan, Henderson, Farabow, Garrett & Dunner, L.L.P.

[57] ABSTRACT

A colposcopic surgical punch instrument includes a hollow tube and a push rod extending through the hollow tube. A handle is coupled to the proximal end of the tube and an actuation lever is pivotally coupled to the handle and the proximal end of the push rod for effecting axial movement of the push rod relative to the tube. A stationary jaw in the form of a die having an open top and bottom is coupled to the distal end of the tube and a movable jaw in the form of a punch is pivotally coupled to the stationary jaw by a tongue and groove arrangement. In one embodiment, the stationary jaw is provided with a pair of ramped projections on its sides and a tab projection on its distal end. A removable plastic sleeve fits over the stationary jaw. The plastic sleeve has an open proximal end and an open top. A pair of holes in the sides of the sleeve engage the ramped projections on the sides of the stationary jaw and a hole in the distal end of the sleeve engages the distal tab on the stationary jaw. The top opening of the sleeve is dimensioned to allow free movement of the movable jaw into and out of the stationary jaw. When attached to the stationary jaw, the sleeve functions as a multiple sample basket beneath the open bottom of the stationary jaw. In another embodiment, the jaw has surface recesses and the sleeve has interior projections.

5 Claims, 5 Drawing Sheets

COLPOSCOPIC BIOPSY PUNCH WITH REMOVABLE MULTIPLE SAMPLE BASKET

This is a division of application, Ser. No. 08/355,057 filed on Dec. 13, 1994 now U.S. Pat. No. 5,643,307.

This application is related to co-owned U.S. application Ser. No. 07/978,249 filed Nov. 18, 1992, application Ser. No. 08/101,190 filed Oct. 3, 1993, and application Ser. No. 08/180,434 filed Jan. 12, 1994, all of which are incorporated by reference herein in their entireties.

BACKGROUND OF THE INVENTION

1. Field of the Invention

The present invention broadly relates to surgical instruments. More particularly, the invention relates to colposcopic biopsy instruments which have a punch end effector with means for collecting multiple biopsy samples.

2. State of the Art

The colposcopic biopsy procedure has become a widely practiced surgical procedure. The colposcope is an optical instrument, similar to an endoscope, which is used in conjunction with an endocervical speculum to examine the cervix. The procedure essentially involves inserting the speculum through the vagina and placing the distal end of the colposcope into the speculum. The speculum is manipulated until the cervix is at a right angle to the light of the colposcope. Upon examination, if abnormality of the cervical tissue is observed, one or several biopsy samples are obtained from one or several cervical locations with the use of a colposcopic biopsy forceps.

Colposcopic biopsy forceps generally include an actuating handle coupled by rods to an end effector assembly. The end effector assembly typically includes a pair of jaws one of which is rotatably coupled to the other, thereby allowing articulation of one of the end effectors relative to the other. The jaws are intended to achieve a cutting action through a punch and die configuration which severs the tissue from the joint by punching the tissue with a sharp edged jaw through a die. The die typically takes the form of a stationary jaw, while the punch takes the form of a movable jaw which rotates relative to the stationary jaw from an open position to a closed position when cutting. Some of these instruments take small, relatively superficial samples unless the practitioner stabilizes the cervix because they tend to slip away from the tissue as the jaws are closed. These instruments often crush rather than cut through the epithelium, often producing an unsatisfactory specimen. Other instruments have serrations on the die which aid in stabilizing the biopsy area. Still other instruments provide tooth-like projections on the punch which effectively stabilize the cervix, but tend to make a very deep cut resulting in excessive bleeding.

When collecting biopsy samples of the cervix, it is very important to record the location from which each sample was taken. The normal procedure is to take one sample, remove the forceps, and deposit the sample in an individual container. The forceps are then reintroduced through the speculum and another sample is taken. Typically, each sample is captured in and by the punch end effector so that it does not fall through the die. This arrangement makes it impossible to take multiple samples since the second sample would either fall through the die end effector or cause the first sample to become dislodged from the punch end effector.

SUMMARY OF THE INVENTION

It is therefore an object of the invention to provide a surgical punch instrument which is capable of collecting multiple cervical tissue samples.

It is also an object of the invention to provide a surgical endoscopic punch instrument which has enhanced strength.

It is another object of the invention to provide a surgical punch instrument which is useful in both single and multiple cervical biopsy collection procedures.

It is a further object of the invention to provide a surgical punch instrument which is easily and quickly adaptable to perform both single and multiple cervical biopsy collection procedures.

In accord with these objects which will be discussed in detail below, the surgical punch instrument of the present invention includes a hollow tube having a proximal and a distal end, a push rod having a proximal and a distal end extending through the hollow tube, a stationary jaw coupled to the distal end of the hollow tube, a movable jaw coupled to the distal end of the push rod and to the stationary jaw, and a removable sleeve which is removably attached to the stationary jaw. The stationary jaw is in the form of a die having an open top and an open bottom and at least one surface engagement means for engaging the removable sleeve. The movable jaw is in the form of a punch and is pivotally coupled to the stationary jaw for movement into and out of the open top of the stationary jaw. A handle is coupled to the proximal end of the tube and an actuation lever is pivotally coupled to the handle and the proximal end of the push rod for effecting axial movement of the push rod relative to the tube, thereby effecting movement of the movable jaw punch into and out of the stationary jaw die.

According to a preferred aspect of the present invention, the removable sleeve is a plastic sleeve which fits over the stationary jaw. The plastic sleeve is provided with an open proximal end, an open top, a closed bottom basket, and at least one means for engaging the stationary jaw. The top opening of the sleeve is dimensioned to allow free movement of the movable jaw into and out of the stationary jaw. When attached to the stationary jaw, the sleeve functions as a multiple sample basket beneath the open bottom of the stationary jaw.

According to one embodiment of the invention, attachment of the sleeve to the stationary jaw is facilitated by providing the sides of the stationary jaw with a pair of ramped projections, the distal end of the stationary jaw with a tab projection, and by providing the sides of the sleeve with a pair of holes which engage the ramped projections on the sides of the stationary jaw and the distal end of the sleeve with a hole which engages the distal tab on the stationary jaw. The engagement of the sleeve with the ramped projections on the jaw prevent it from inadvertently slipping off the jaw in the distal direction. The engagement of the distal end of the sleeve with the distal tab prevents the sleeve from being deflected away from the bottom of the jaw. The plastic sleeve is preferably somewhat elastic so than it can be attached to and removed from the jaw without breaking, but not so elastic that it can be inadvertently detached from the jaw during a biopsy procedure. In another embodiment of the invention, the sleeve has inwardly extending projections and the jaw has external recesses which receive and engage the inwardly extending projections on the sleeve.

Additional objects and advantages of the invention will become apparent to those skilled in the art upon reference to the detailed description taken in conjunction with the provided figures.

DETAILED DESCRIPTION OF THE PREFERRED EMBODIMENTS

Figures 1, 1A:
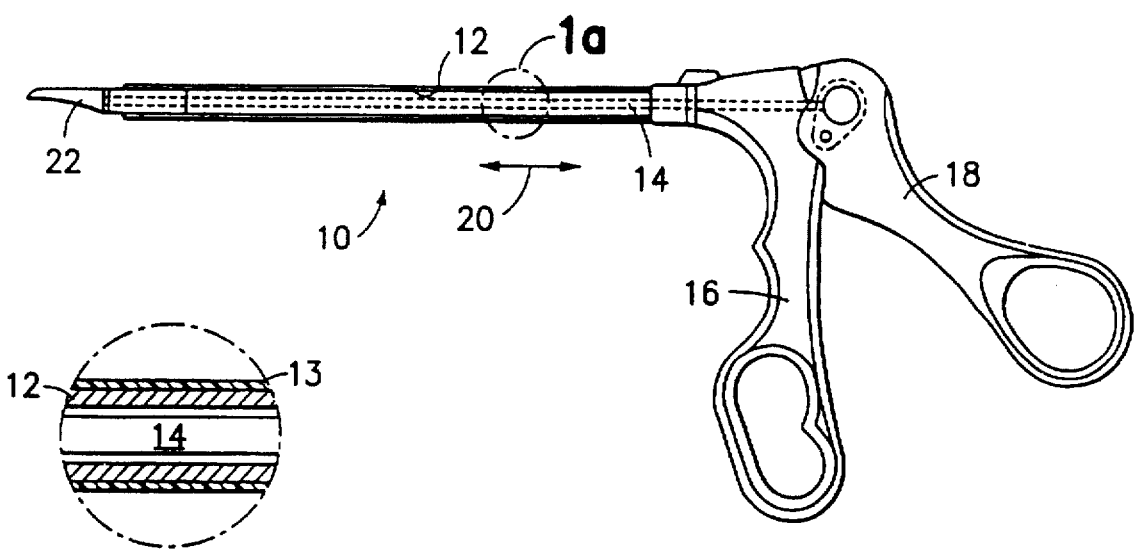
FIG. 1 is partially transparent side elevation view of a surgical punch instrument according to the invention.
FIG. 1a is an enlarged cross-sectional view of an indicated portion of the instrument of FIG. 1.
Figure 2:
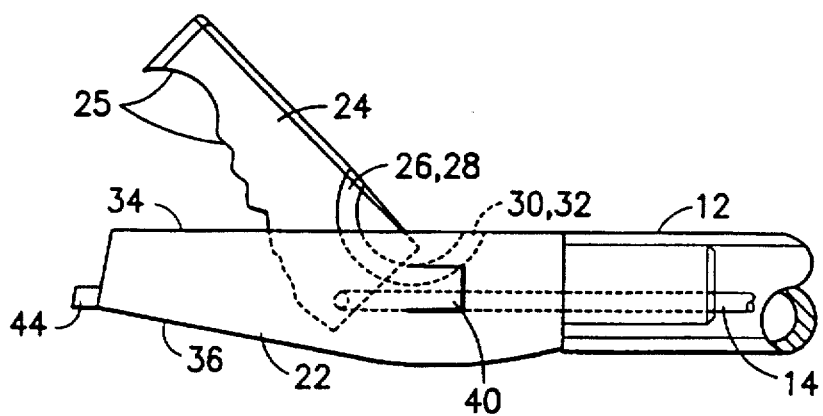
FIG. 2 is a partially transparent enlarged broken side elevation view of the distal end of a first embodiment of the instrument with the jaws in the open position.
Figure 3:
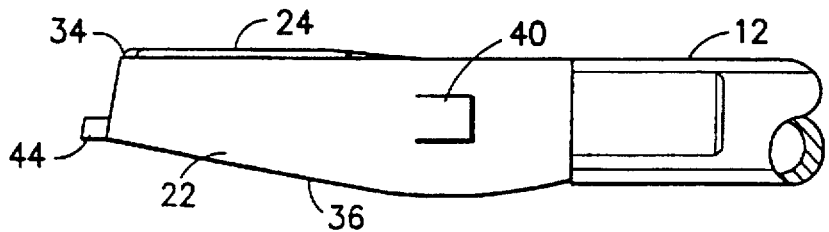
FIG. 3 is a view similar to FIG. 2 with the jaws in the closed position.
Figure 4:
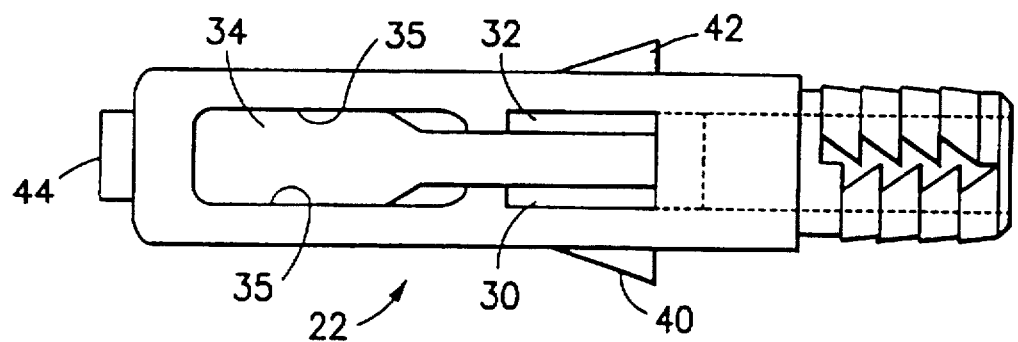
FIG. 4 is a top plan view of the first embodiment of the stationary jaw according to the invention.

Referring now to FIGS. 1 through 4, the surgical punch instrument 10 according to the invention resembles an arthroscopic punch and includes a hollow tube 12 and a push rod 14 which extends through the tube 12. The tube 12 may optionally be provided with an insulating shrink wrap covering 13 as described in the previously incorporated applications. The proximal end of the tube 12 is coupled to a handle 16 and the proximal end of the push rod 14 is coupled to a lever 18 which is pivotally coupled to the handle 16. Movement of the lever 18 relative to the handle 16 therefore imparts a reciprocal axial movement to the rod 14 relative to the tube 12 as shown by the arrows 20 in FIG. 1.

As described in detail in the co-owned related applications cited above, a stationary jaw 22 is coupled to the distal end of the tube 12, and a movable jaw 24 is coupled to the distal end of the push rod 14. The movable jaw 24 has a pair of arcuate grooves 26, 28 and the stationary jaw 22 has a pair of arcuate flanges 30, 32 which engage the grooves 26, 28 on the movable jaw 24. The stationary jaw 22 has an upper opening 34 and a lower opening 36. The movable jaw 24 is therefore movable into and out of the upper opening 34 of the stationary jaw 22 by action of the lever 18. The movable jaw 24 has sharp cutting teeth 25 which coact with the inner surface 35 of the upper opening 34 of the stationary jaw 22 when the movable jaw is moved from the open position shown in FIG. 2 to the closed position shown in FIG. 3. The jaws thus act like a punch and die to cut tissue and pieces of cut tissue are freely removable from the jaws through the bottom opening 36 of the stationary jaw 22.

According to a first embodiment of the present invention, the outer surface of the stationary jaw 22 is provided with a pair of outwardly extending ramped projections 40, 42 and a outwardly extending distal tab projection 44. The ramped projections 40, 42 are preferably located on the sides of the jaw 22 proximal of the upper and lower openings 34, 36 and ramp outward in the proximal direction. The distal tab projection 44 preferably extends from the distal end of the jaw 22 in a direction substantially parallel to the longitudinal axis of the jaw, although it may also be angled if desired.

Figure 5:
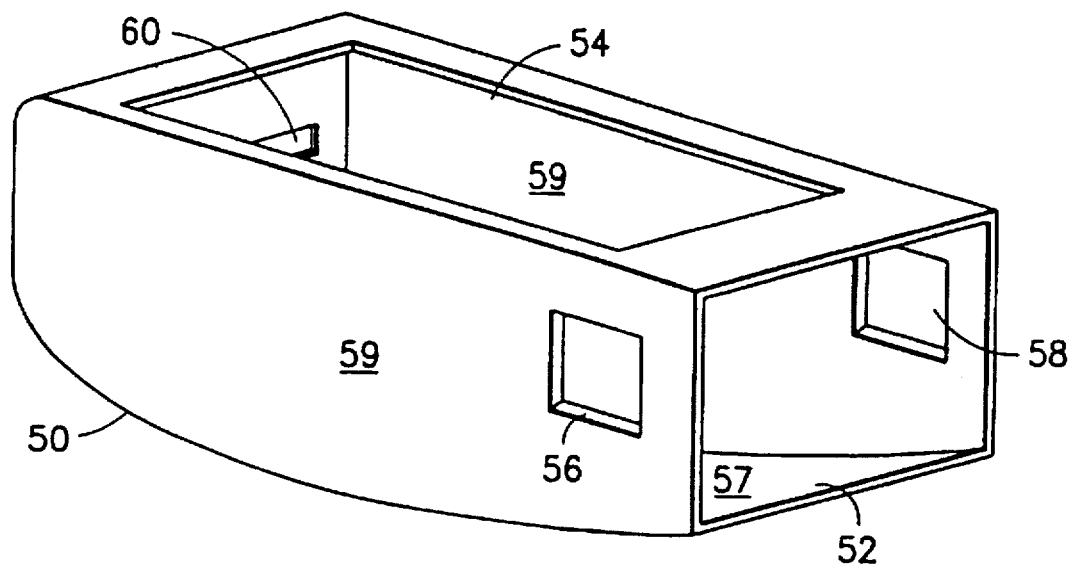
FIG. 5 is an enlarged perspective view of a first embodiment of the plastic sleeve according to the invention.
Figure 6:
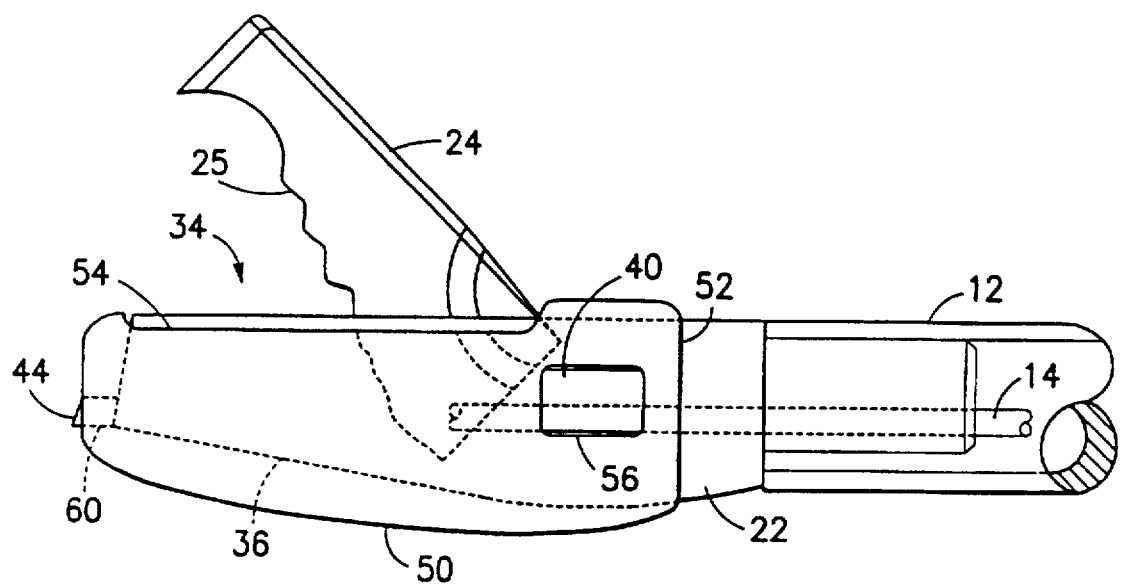
FIG. 6 is a view similar to FIG. 2 with a plastic sleeve attached to the stationary jaw.
Figure 7:
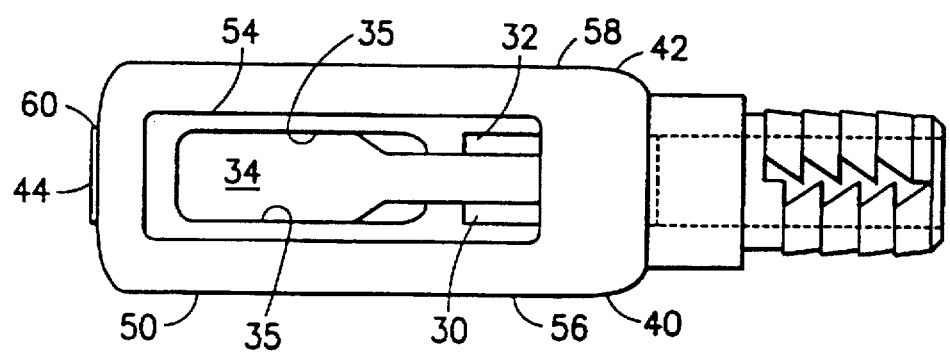
FIG. 7 is a view similar to FIG. 4 with a plastic sleeve attached to the stationary jaw.
Figure 8:
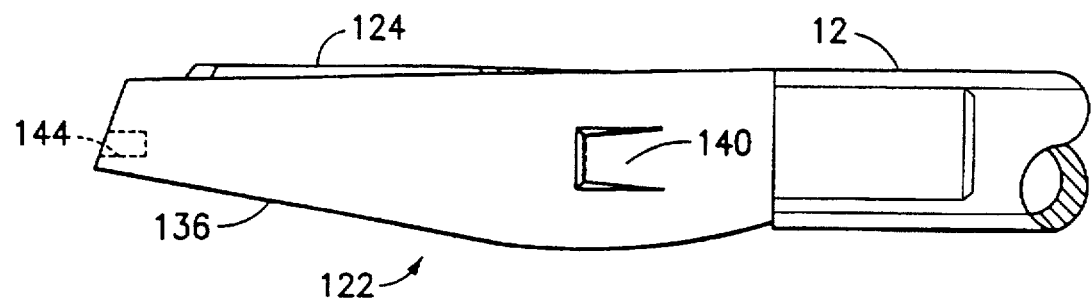
FIG. 8 is a view similar to FIG. 3, but of a second embodiment of the invention.
Figure 9:
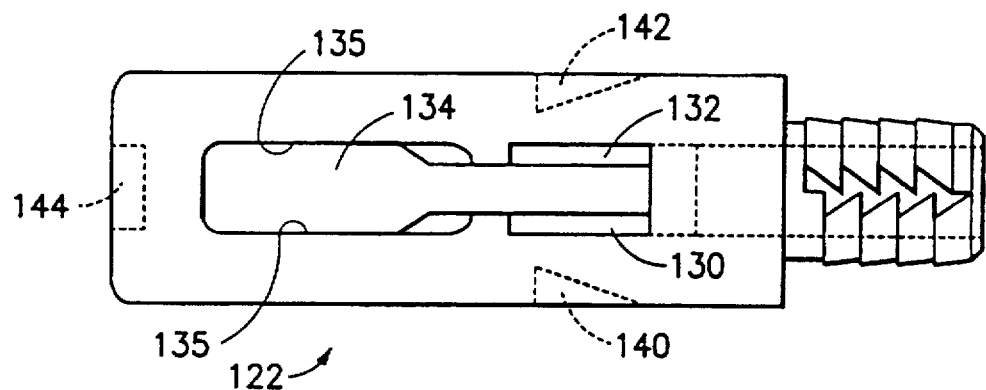
FIG. 9 is a view similar to FIG. 4, but of the second embodiment of the invention.
Figure 10:
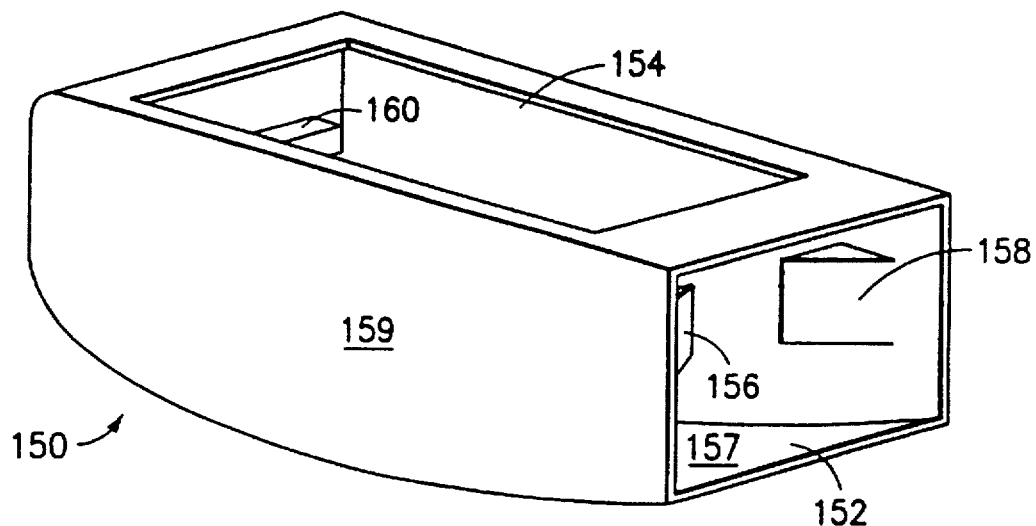
FIG. 10 is a view similar to FIG. 5 of a second embodiment of the plastic sleeve according to the invention.
Figure 11:
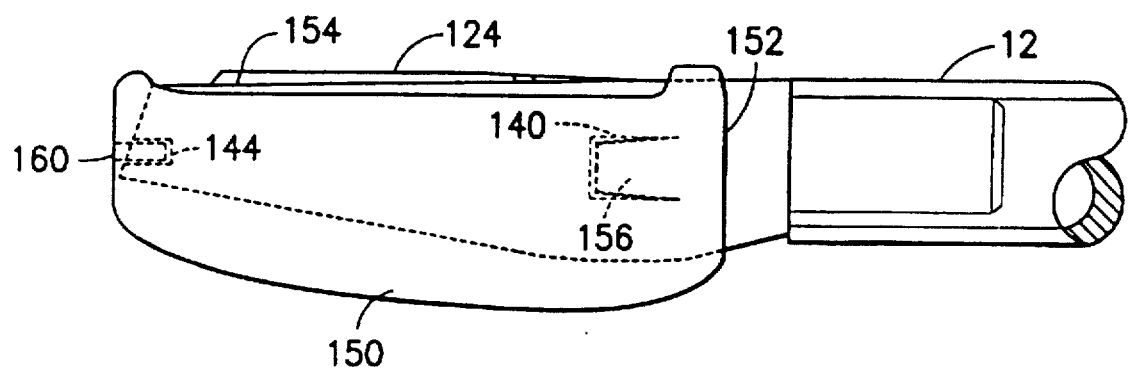
FIG. 11 is a view similar to FIG. 6, but of the second embodiment of the invention, and with the movable jaw in the closed position.
Figure 12:
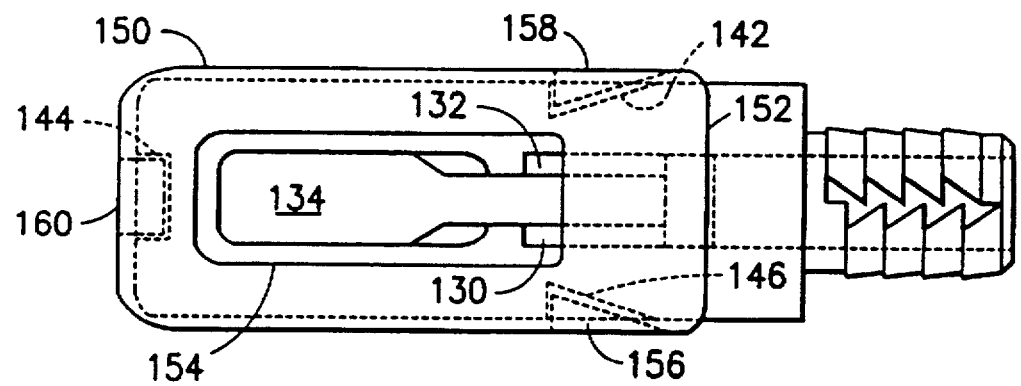
FIG. 12 is a view similar to FIG. 7, but of a second embodiment of the invention.

Turning now to FIGS. 5–7, a first embodiment of a removable plastic sleeve 50 is seen to be designed to fit over the stationary jaw 22. The sleeve 50 has a proximal opening 52, an upper opening 54, a pair of side openings 56, 58, and a distal end opening 60. The proximal opening 52 of the plastic sleeve 50 is dimensioned to allow the sleeve 50 to slide over the jaws 22, 24 when they are in the closed position. The upper opening 54 is dimensioned to allow the movable jaw 24 to move freely into and out of the stationary jaw 22 when the sleeve 50 is attached to the jaw 22. The side openings 56, 58 of the sleeve 50 are located and dimensioned to engage the ramped projections 40, 42 and the distal end opening 60 is located and dimensioned to engage the distal tab projection 44. When the sleeve 50 is attached to the jaw 22 as shown in FIGS. 6 and 7, the bottom opening 36 of the jaw 22 is covered by the sleeve 50 so that cut tissue, e.g. a biopsy sample, cannot fall out of the bottom opening 36 in the jaw 22. The sleeve 50 thereby acts as a collection basket so that multiple samples may be collected. The side openings 56, 58 engage the ramped projections 40, 42 so that the sleeve 50 cannot inadvertently slide off the jaw 22 and the distal end opening 60 engages the distal tab projection 44 so that the sleeve 50 cannot be inadvertently deflected away from the bottom of the jaw 22. It will be appreciated that the dimensions of the sleeve 50 should be such that the sleeve fits snugly over the jaw 22. Moreover, those skilled in the art will appreciate that the sleeve 50 should have a sufficient amount of elasticity so that it can slide over the ramped projections 40, 42 and still be removable from the jaw 22 without breaking; but not so much elasticity that the sleeve can inadvertently slide off the jaw during a biopsy procedure.

If desired, the sleeve 50 may be provided with small holes (not shown) on its bottom surface 57 and one or more of its side surfaces 59. Such holes would be dimensioned to guarantee that biopsy samples would not inadvertently fall out of the sleeve 50, but would be large enough to permit extraction of biopsy samples while the sleeve 50 is fixed on the jaw 22 via tweezers or a hook.

FIGS. 8 through 12 show a second embodiment of the invention. The stationary jaw 122 according to the second embodiment is similar to the jaw 22 of the first embodiment with similar reference numerals denoting similar features. The second embodiment of the jaw 122 has a pair of side recesses or indents 140, 142 rather than ramped projections as shown in the first embodiment. Jaw 122 is also provided with a distal recess or indent 144 rather than a distal tab extension as shown in the first embodiment. The movable jaw 124 used with the stationary jaw 122 is virtually identical to the movable jaw 24 described above.

In the second embodiment of the invention, the removable plastic sleeve 150 is similar to the sleeve 50 of the first embodiment with similar reference numerals denoting similar features. The sleeve 150 has a pair of ramped inner projections 156, 158 on the side surface 159 rather than the side openings as shown in the first embodiment. The ramped projections 156, 158 are located near the proximal opening 152 of the sleeve 150 and ramp inward in the proximal direction. The distal end of the sleeve 150 has an inward extending tongue 160 rather than a distal end opening as shown in the first embodiment.

From the foregoing, those skilled in the art will appreciate that the second embodiment of the invention operates in substantially the same manner as the first embodiment except that projections and recesses have been exchanged with each other. It will further be appreciated that the engaging means 40, 42, 44, 140, 142, 144 on the jaw 22, 122 may be any combination of projection and/or recess. Similarly, the engaging means 56, 58, 60, 156, 158, 160 on the sleeve 50, 150 may also be any combination of projection and/or recess. It is only necessary that the projections on one of the jaw and sleeve engage the recesses on the other of the jaw and sleeve.

The operation of the punch instrument in a colposcopic procedure is as follows. The colposcopic examination is commenced in the normal way with the insertion of the speculum and the colposcope. The practitioner observes the cervix and determines whether one or more biopsy samples are to be taken. If multiple samples are to be taken from a single location, the sleeve 50, 150 is attached to the instrument as described above, and the instrument is inserted through the speculum under the observation of the colposcope. The practitioner locates the portion of cervical tissue requiring biopsy, opens the jaws of the instrument and brings them into engagement with the tissue. As the jaws are closed, through operation of the lever 18, the sharp cutting teeth 25 stabilize the biopsy area and pull the tissue into the upper opening 34 of the stationary jaw 22. The teeth 25 coact with the inner surface 35 of the opening 34 and a tissue sample is severed from the cervix. The tissue sample is pushed by the movable jaw 24 into the stationary jaw 22 where it resides in the opening 360. To take a second sample, the procedure is repeated and the second sample pushes the first sample further into the sample basket formed by the sleeve 50, 150. Additional samples may be taken as required. After the required samples have been taken, the instrument is removed from the speculum. The samples may be recovered in several ways. First, the sleeve 50, 150 can be removed from the instrument and the samples taken. Second, in the case of a sleeve having holes, the samples may be grapsed by a tweezers or the like, and forcibly removed through the holes. Third, the punch instrument with the jaw in an open position can be turned upside down and jostled until the samples fall out. It will be appreciated that the instrument can be used with or without the sample basket depending on the needs of the practitioner.

There has been described and illustrated herein a surgical punch instrument having a removable biopsy sample basket. While particular embodiments of the invention have been described, it is not intended that the invention be limited thereto, as it is intended that the invention be as broad in scope as the art will allow and that the specification be read likewise. Thus, while particular engaging projections on the stationary jaw or the removable sleeve have been disclosed, it will be appreciated that other projections in other locations could be utilized. Also, while particular holes or recesses on the stationary jaw or the removable sleeve have been shown, it will be recognized that other types of holes or recesses in other locations could be used with similar results obtained. For example, since it is the primary purpose of the sleeve to cover the open bottom of the jaw, the sleeve and jaw may be configured so that the sleeve mounts vertically from below the jaw rather than sliding horizontally on to the jaw. It will thus be appreciated that the sleeve can be shaped like a basket or a scoop. In any case, the sleeve should be coupled to the jaw at at least two locations for stability. Moreover, while particular configurations have been disclosed in reference to tongue and groove coupling of the jaw members, it will be appreciated that other configurations could be used as well. Furthermore, while the jaw and sleeve have been disclosed as having three engagement means, it will be understood that different numbers of engagement means can achieve the same or similar function as disclosed herein. It will therefore be appreciated by those skilled in the art that yet other modifications could be made to the provided invention without deviating from its spirit and scope as so claimed.

We claim:

1. A removable biopsy sample basket for use with a surgical punch instrument having a first jaw with an open top and an open bottom and at least one exterior engaging means for engaging a removable sleeve and a movable jaw pivotally coupled to the first jaw, said removable sample basket comprising:

a sleeve having a proximal opening, a top opening, an exterior wall extending distally from said proximal opening and at least one interior engaging means for engaging the exterior engaging means of the first jaw, said interior engaging means being located on exterior side wall and being dimensioned to lockingly engage the exterior engaging means of the first jaw when said sleeve is moved proximally over the first jaw.

2. A removable biopsy sample basket for use with a surgical punch instrument having a first jaw with an open top and an open bottom and at least one exterior engaging means for engaging a removable sleeve and a movable jaw pivotally coupled to the first jaw, said removable sample basket comprising:

a sleeve having a proximal opening, a top opening, an exterior wall extending distally from said proximal opening and at least one interior engaging means for engaging the exterior engaging means of the first jaw, wherein said at least one interior engaging means comprises a pair of side openings in said exterior wall for engaging side projections on the first jaw.

3. A removable biopsy sample basket according to claim 2, wherein:

said at least one interior engaging means further comprises a distal opening for engaging a distal tab on the first jaw.

4. A removable biopsy sample basket for use with a surgical punch instrument having a first jaw with an open top and an open bottom and at least one exterior engaging means for engaging a removable sleeve and a movable jaw pivotally coupled to the first jaw, said removable sample basket comprising:

a sleeve having a proximal opening, a top opening, an exterior wall extending distally from said proximal opening and at least one interior engaging means for engaging the exterior engaging means of the first jaw, wherein said at least one interior engaging means comprises a pair of interior side projections for engaging side recesses on the first jaw, said side projections being ramped in the proximal to distal direction.

5. A removable biopsy sample basket according to claim 4, wherein:

said at least one interior engaging means further comprises an interior distal tongue for engaging a distal end recess on the first jaw.

* * * * *